US00PP26895P2

(12) United States Plant Patent
Hansen

(10) Patent No.: US PP26,895 P2
(45) Date of Patent: Jun. 28, 2016

(54) ***SEDUM* PLANT NAMED 'LIME TWISTER'**

(50) Latin Name: ***Sedum* hybrid**
Varietal Denomination: Lime Twister

(71) Applicant: Christopher M. Hansen, Holland, MI (US)

(72) Inventor: Christopher M. Hansen, Holland, MI (US)

( * ) Notice: Subject to any disclaimer, the term of this patent is extended or adjusted under 35 U.S.C. 154(b) by 106 days.

(21) Appl. No.: 14/121,636

(22) Filed: Sep. 30, 2014

(51) Int. Cl.
*A01H 5/02* (2006.01)

(52) U.S. Cl.
USPC ..... Plt./479

(58) Field of Classification Search
USPC ..... Plt./479
See application file for complete search history.

*Primary Examiner* — Annette Para
(74) *Attorney, Agent, or Firm* — Penny J. Aguirre

(57) ABSTRACT

A new cultivar of *Sedum* plant named 'Lime Twister' characterized by its spreading mound, ground-cover plant habit, its thumbnail-sized leaves that are lime-green in color with wide cream-white colored margins, its green and white variegated leaves with red picotee margins during cool spring and fall weather, its well-branched and vigorous growth habit; producing numerous lateral branches and growth crowns on a single plant, its fast and easy rooting; forming roots in 15 days, which is unusually fast for other variegated *Sedum* cultivars, and its persistent vigorous growth and colorful foliage lasting from early spring through the hot summer months with over 16 weeks of colorful variegated foliage.

2 Drawing Sheets

Botanical classification: *Sedum* hybrid.
Variety denomination: 'Lime Twister'.

CROSS REFERENCE TO A RELATED APPLICATION

This application is co-pending with a U.S. Plant Patent Application filed for a plant derived from the same breeding program that is entitled *Sedum* Plant Named 'Lime Zinger' (U.S. Plant Pat. No. 24,632).

BACKGROUND OF THE INVENTION

The present invention relates to a new and distinct cultivar of *Sedum* plant, botanically of hybrid origin and known as *Sedum* 'Lime Twister' referred to hereinafter by its cultivar name, 'Lime Twister'. The new cultivar of *Sedum* is a hardy herbaceous perennial grown for use as a landscape and container plant and is particularly suitable as a groundcover.

The Inventor discovered the new cultivar in February of 2014 as a naturally occurring branch mutation of *Sedum* 'Lime Zinger' in a 128-cell plug tray at his nursery in Hudsonville, Mich., USA.

Asexual propagation of the new cultivar was first accomplished by stem tip cuttings in April of 2014 in Hudsonville, Mich. Asexual propagation by stem tip cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Lime Twister' as a unique cultivar of *Sedum*.

1. 'Lime Twister' exhibits a spreading mound, ground-cover plant habit.

2. 'Lime Twister' exhibits consistent thumbnail-sized leaves that are lime-green in color with wide cream-white colored margins.
3. 'Lime Twister' exhibits green and white variegated leaves with red picotee margins during cool spring and fall weather.
4. 'Lime Twister' exhibits a well-branched, vigorous growth habit, producing numerous lateral branches and growth crowns on a single plant.
5. 'Lime Twister' exhibits fast and easy rooting, forming roots in 15 days, which is unusually fast for variegated *Sedum* cultivars.
6. 'Lime Twister' exhibits persistent vigorous growth and colorful foliage lasting from early spring through the hot summer months with over 16 weeks of colorful variegated foliage.

The parent of 'Lime Twister', 'Lime Zinger' differs from 'Lime Twister' in having leaves that are solid lime-green in color. 'Lime Twister' can be most closely compared to the *Sedum spurium* cultivar 'Tricolor' (not patented) and the *Sedum sieboldii* cultivar 'Mediovariegata' (not patented). 'Tricolor' is similar to 'Lime Twister' in having a groundcover plant habit and in having green and creamy-white variegated foliage. 'Tricolor' differs from 'Lime Twister' in having a less vigorous growth habit, in having leaves that are smaller in size, in having a dormant period during hot summer months, and in having leaves that are susceptible to burning in intense July and August sun. 'Mediovariegata' is similar to 'Lime Twister' in having a groundcover plant habit and in having variegated foliage. 'Mediovariegata' differs from 'Lime Twister' in having leaves with creamy-white centers and green colored margins, in having a very high reversion rate, in being slow to root, and in having a very slow growth habit.

BRIEF DESCRIPTION OF THE DRAWINGS

The accompanying colored photographs illustrate the overall appearance and distinct characteristics of the new *Sedum*. The photographs were taken of a plant about 3 months in age as grown outdoors in a 1-gallon container in Hudsonville, Mich.

The photograph in FIG. 1 provides a view of the plant habit of 'Lime Twister'.

Figure 1:
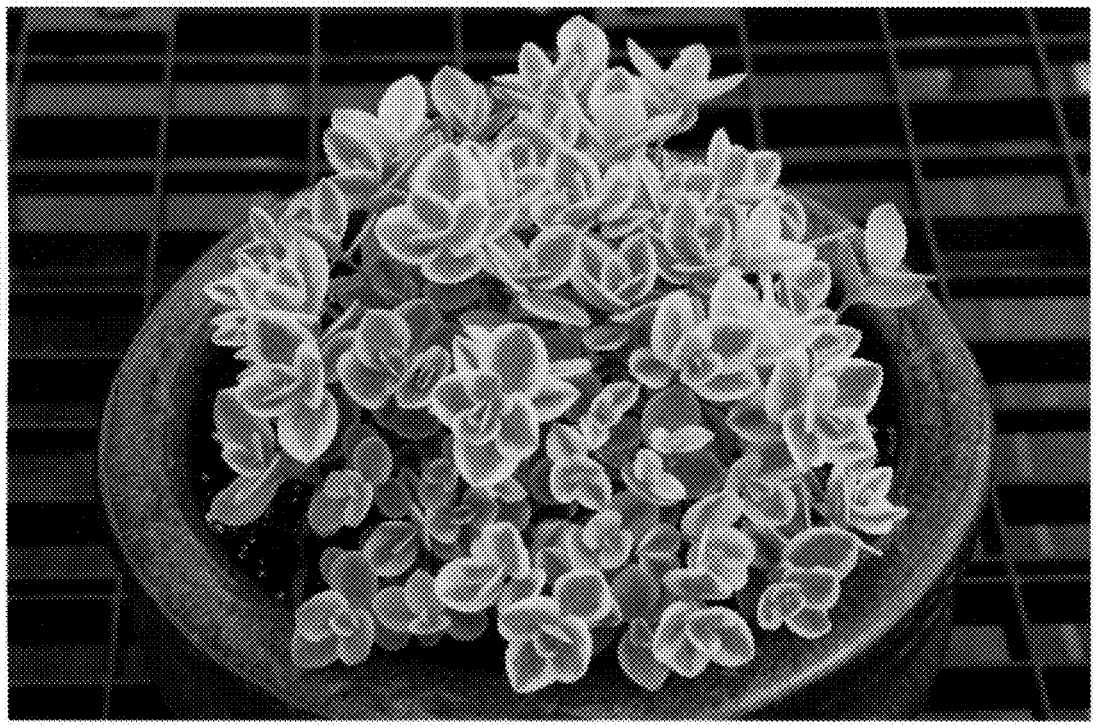
Figure 2:
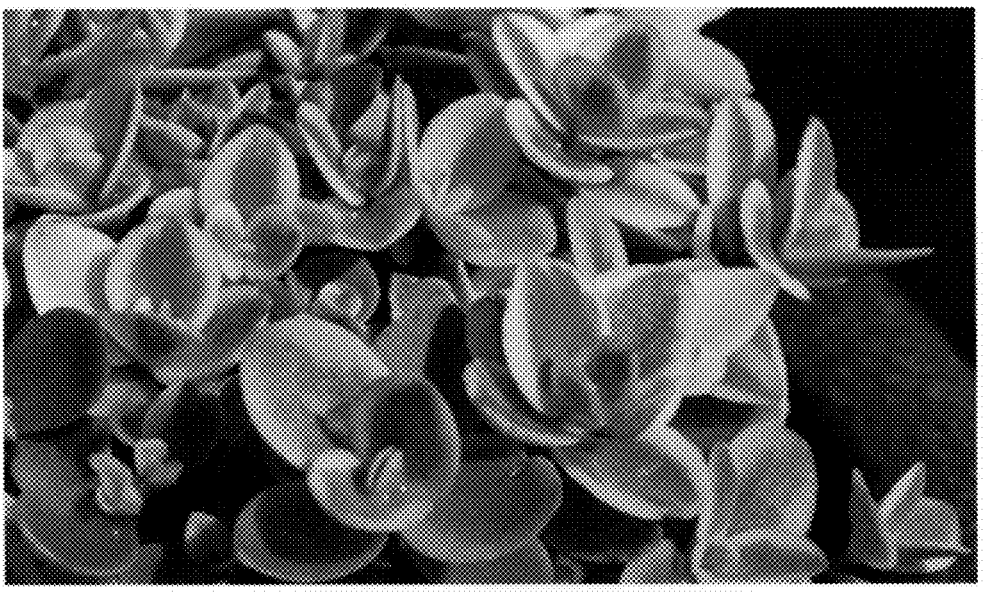

The photograph in FIG. 2 provides a close-up view of the foliage of 'Lime Twister'.

Figure 3:
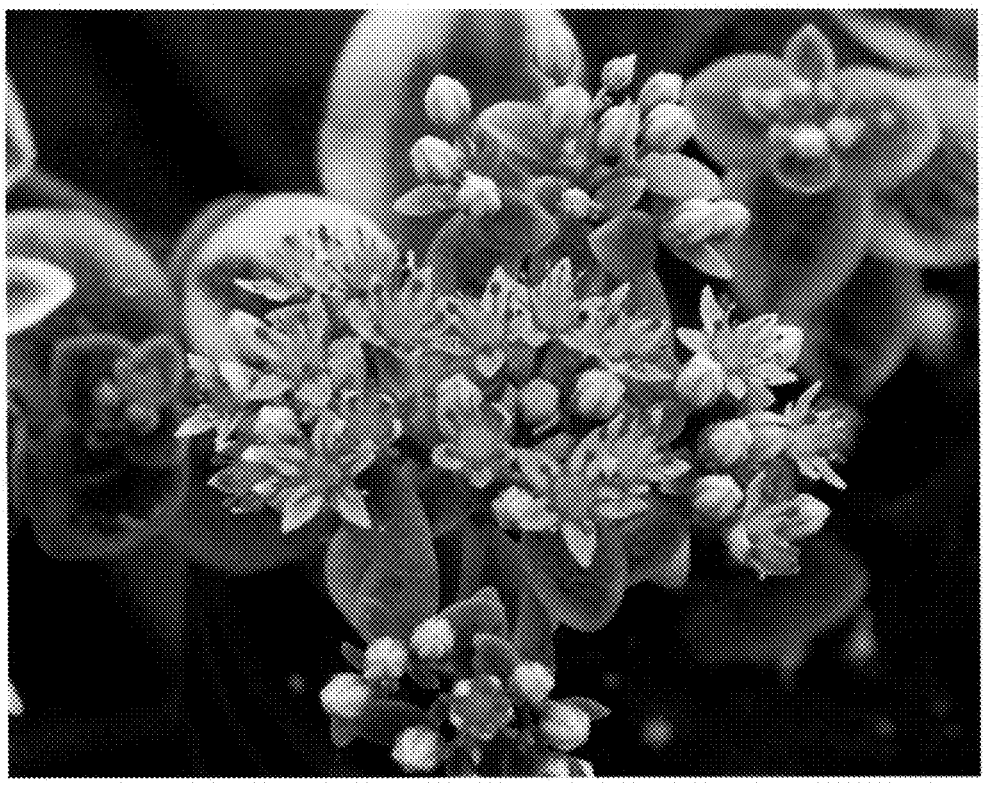

The photograph in FIG. 3 provides a close-up view of the inflorescences of 'Lime Twister'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 3 month-old plants of 'Lime Twister' as grown outdoors in one-gallon containers in Hudsonville, Mich. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period*.—3 to 4 weeks in late summer in Hudsonville, Mich.

*Plant type*.—Herbaceous perennial.

*Plant habit*.—Spreading mound, ground-cover, well-branched.

*Height and spread*.—Reaches about 15 cm in height and about 45 cm in spread.

*Hardiness*.—At least hardy in U.S.D.A. Zones 4 to 9.

*Diseases pest*.—Resistance to *sedum* leaf scorch has been observed.

*Root description*.—Fibrous.

*Propagation*.—Tip stem cuttings.

*Growth rate*.—Vigorous, forms dozens of offshoots from a single plant.

*Rooting*.—Roots are initiated in about 15 days.

Stem description:

*Stem shape*.—Oval.

*Stem size*.—An average of 12 cm in length and 2 mm in width, lateral branches an average of 8 mm in length and 2 mm in width.

*Internode length*.—Average of 1 cm with terminal leaves whorled (<0.5 mm).

*Stem color*.—138A suffused with 184A.

*Stem surface*.—Glabrous.

*Branching habit*.—Numerous basal and lateral branches.

Foliage description:

*Leaf shape*.—Ovate-orbicular.

*Leaf division*.—Simple.

*Leaf arrangement*.—Whorled (sometimes opposite).

*Leaf base*.—Truncate.

*Leaf apex*.—Broadly acute-rounded.

*Leaf venation*.—Not conspicuous, color matched leaf color.

*Leaf margins*.—Entire.

*Leaf attachment*.—Sessile.

*Leaf orientation*.—Nearly horizontal to slightly upward, slightly cupped.

*Leaf texture*.—Thick, succulent.

*Leaf surface*.—Glandular and slightly glaucous.

*Leaf color*.—Spring upper and lower surface; 138A at the center and 150D towards the edge with very thin picotee margins 71B, mid-summer and fall upper and lower surface, 138A at the center and margins a blend of 150D and 155C.

*Leaf size*.—Average of 1.8 cm in length and 1.6 cm in width.

Flower description:

*Inflorescence type*.—Dense, slightly rounded cymes with an average of 5 terminal forked branches at terminus and upper lateral nodes.

*Inflorescence size*.—An average of 4 cm in diameter and 3 cm in depth (inclusive of all branches per stem).

*Lastingness of inflorescence*.—About one month.

*Flower type*.—Perfect, spreading, 5-starred.

*Flower number*.—An average of 10 flowers per branched cyme, about 50 flowers per stem.

*Flower fragrance*.—None.

*Flower buds*.—Ovate in shape, about 3 mm length and 2 mm in width, ribbed surface, color; a blend of 155C and 63B.

*Flower size*.—Average of 3 mm in depth and 5 mm in diameter.

*Peduncles*.—Slightly oval in shape, an average of 1.2 cm in length and 1 mm in width, secondary average 4 mm in length and 0.9 mm in width, a blend of 138A and 144A in color, glabrous surface, peduncle leaves; an average of 3 per individual cyme, ovate to orbicular in shape, an average of 9 mm length and 7 mm in width, a blend of 137A and 138C in color with 139A at the center with thin margin of 138B, glandular and slightly glaucous on both surfaces.

*Pedicels*.—Slightly oval in shape, an average of 2 cm in length and 0.8 mm in width, 138A in color, glabrous surface.

*Calyx*.—5-parted fused to tubular base, tips held nearly upright, about 3 mm in length and 2 mm in width.

*Sepals*.—5, tube; about 1 mm in length and 2 mm in width, 138A in color, tips about 2 mm in length and 0.7 cm in width, lanceolate in shape, 138A in color with margins 145D on both surfaces, entire margin, narrowly acute apex, fused base, glaucous on both surfaces.

*Petals*.—5, spreading, 3 mm in length and 1.1 mm in width, elliptic in shape, cuneate base, acute apex, entire margin, color of inner and outer surfaces when opening; 155A and tinged with 63B, color when mature; 155A tinged with 65A, becoming dry and upright and 155A very lightly infused with 65A, translucent, glabrous on both surfaces.

Reproductive organs:

*Pistils*.—5, showy, held erect, about 3.5 mm in length 1 mm in width, stigma; 0.2 mm in width and 65A to 65D in color, style; 3.5 mm in length, 1 mm in width, lanceolate in shape and N155C in color, ovary; small, single celled and translucent in color.

*Stamens*.—10, about 1.5 mm in length, filament; very fine and 65A in color, anther; basified, about 0.5 mm in length and width, a mix of 202A and 202D in color, pollen is moderate in quantity and about 11D in color.

*Fruit*.—Fruit and seed production has not been observed.

It is claimed:

1. A new and distinct variety of *Sedum* plant named 'Lime Twister' as described and illustrated herein.

* * * * *